United States Patent [19]

Smith

[11] 4,262,196
[45] Apr. 14, 1981

[54] CONTAINER INSPECTION APPARATUS

[75] Inventor: Robert J. Smith, Florissant, Mo.

[73] Assignee: Barry-Wehmiller Company, St. Louis, Mo.

[21] Appl. No.: 55,614

[22] Filed: Jul. 9, 1979

[51] Int. Cl.³ .............................................. G01V 9/04
[52] U.S. Cl. ................................. 250/223 B; 356/240
[58] Field of Search .................... 250/223 B, 216, 234, 250/235, 236; 209/522–526; 356/240

[56] References Cited
U.S. PATENT DOCUMENTS

| 3,191,773 | 6/1965 | Wyman | 250/223 B |
| 3,283,898 | 11/1966 | Calhoun | 356/240 |

Primary Examiner—David C. Nelms
Attorney, Agent, or Firm—Gravely, Lieder & Woodruff

[57] ABSTRACT

Apparatus for inspecting containers for foreign matter so as to insure the same being free of such matter that could affect the contents when the containers are filled, such apparatus incorporating an inspection system in which a prism is able to rotate non-collimated light without introducing distortion since it does not depend on plane wave fronts and is thus able to greatly expand the field of view, thereby providing more dependable detection of foreign matter at the center and in the peripheral areas of container bottoms and lower side walls.

8 Claims, 9 Drawing Figures

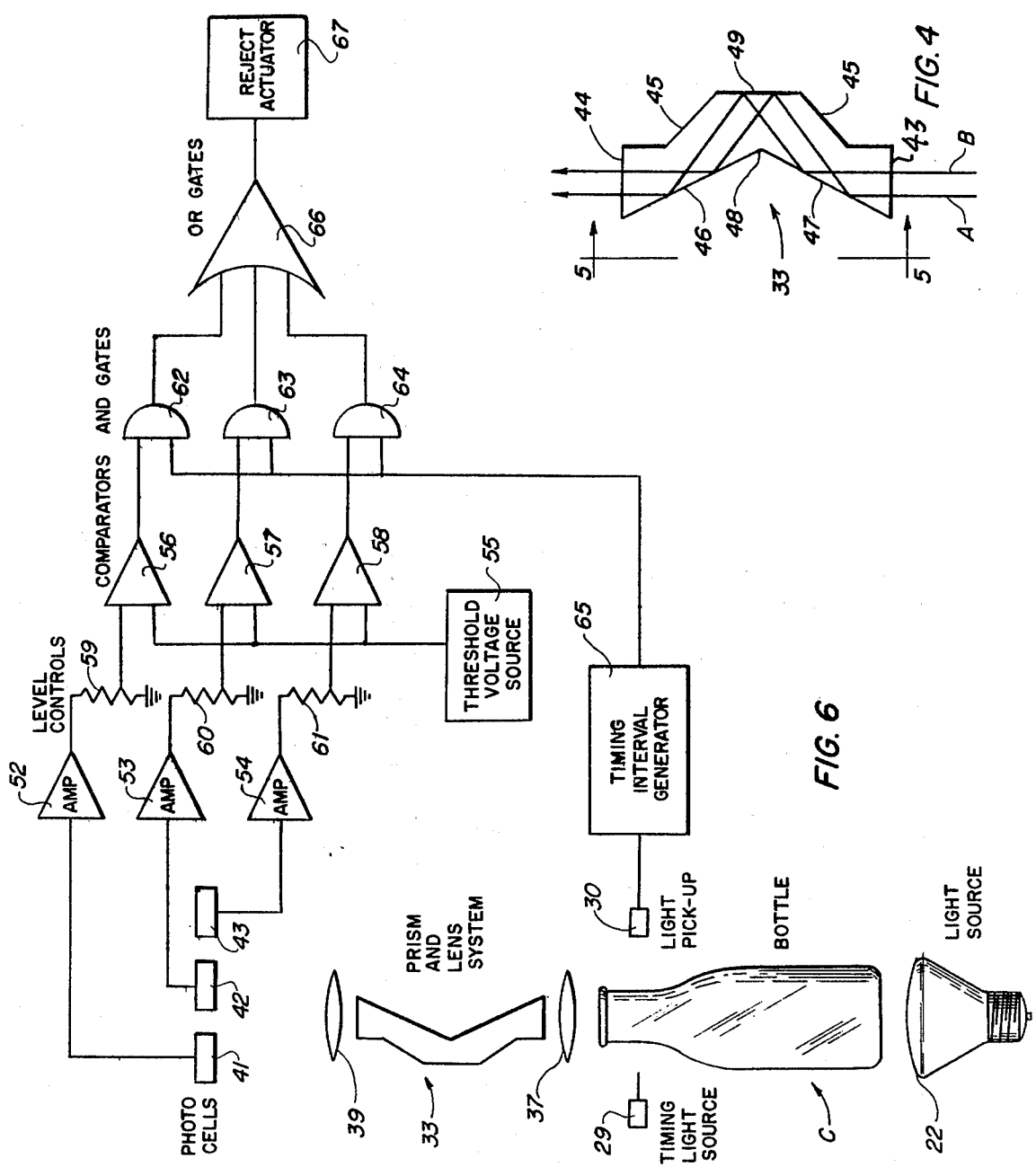

CONTAINER INSPECTION APPARATUS

BACKGROUND OF THE INVENTION

In the handling of containers preparatory to filling them, whether it is a beverage or food stuffs, it is necessary to inspect the containers for foreign matter and to be sure nothing is inside that would allow contamination of the contents. Apparatus for inspecting the interior of containers includes those which have probes to enter the container, and those which inspect from the outside with the aid of light or radiant energy.

Current systems for handling containers of the above classes require inspection means capable of performing the interior inspection while the containers are in motion of the order of up to 800 containers per minute passing the inspection station. This fast acting capability eliminates the types of inspection devices which require each container to stop during the inspection interval, though rotation in the stopped position may be carried out. The latter types of inspection apparatus include those disclosed in Mathias U.S. Pat. No. 3,267,796 of Aug. 23, 1966; Mathias U.S. Pat. No. 3,355,980 of Dec. 5, 1967; Sorbie U.S. Pat. No. 3,327,849 of June 27, 1967; Kidwell U.S. Pat. No. 3,479,514 of Nov. 18, 1969; and Bentley U.S. Pat. No. 2,943,531 of July 5, 1960.

The background patents pertaining to the general arrangement of apparatus for inspecting containers while in movement is exemplified in Wyman U.S. Pat. No. 3,191,773 of June 29, 1965; Gulliksen U.S. Pat. No. 2,265,037 of Dec. 2, 1941; Gender et al U.S. Pat. No. 3,631,255 of Dec. 28, 1971; Babunovic et al U.S. Pat. No. 3,629,595 of Dec. 21, 1971; Stogoff U.S. Pat. No. 1,926,824 of Sept. 12, 1933; Calhoun et al U.S. Pat. No. 3,349,906 of Oct. 31, 1967; and British Pat. No. 905,729 of Sept. 12, 1962.

In addition to the foregoing background disclosures, prismatic devices for various uses have been disclosed in light transmitting cases in such nonanalagous background art as Gould U.S. Pat. No. 2,231,186 of Feb. 11, 1941; Scott U.S. Pat. No. 2,513,367 of July 4, 1950; and Miller U.S. Pat. No. 2,939,962 of June 7, 1960. The general type of prism device employed in the present invention has been disclosed in a military standards handbook for optical design No. MIL-HDBK-141 dated Oct. 5, 1962, at page 13–37 where a typical reversion prism has been shown in FIG. 13.55. This prism may also be designated as a "K" prism.

In the case of each of the disclosures covered by the above enumerated patents and the publication, the prism devices leave a great deal to be desired in the inability to perform the necessary inspection of the complete bottom and lower side walls of containers, and as a result a resort has been directed toward the use of such inspection apparatus as that disclosed by Richardson U.S. Pat. No. 2,798,605 of July 9, 1957, wherein a plurality of container side video inspecting devices, not only look into the containers but also look at the side wall thereof.

BRIEF DESCRIPTION OF THE INVENTION

The present invention is directed to inspection of transparent or translucent containers moving on high speed conveyor means and exposed to being inspected by the use of a reversion prism for presenting an image of the interior of each container on a photosensitive array which then develops response to changes in the light intensity effected by the presence of foreign matter.

It is an object of the present invention to provide inspection apparatus which does not depend on a plane wave fronts, i.e., collimated light in order to rotate the image of the bottom and side wall area of transparent or translucent containers, thereby eliminating certain restrictions in the use of objective lenses so that the field of view can be greatly expanded, and so that uniformity of image brightness is not so dependent on precise alignment of container with the optical system axis.

A further object of the present invention is to improve the foreign matter detection capability in peripheral areas of open mouth containers, and particularly to obtain improved detection capability for relatively large diameter short length containers.

A further object of the present invention is to provide apparatus capable of improving the detection of foreign matter in containers and breaks or other defects in the lower side wall region of the container.

A still further object of the present invention is to provide inspection apparatus utilizing the ability of a reversion prism to rotate non-collimated light without introducing distortion, and to employ objective lenses to keep light centered in an optical system where the light source is located in an off-axis position, or the container is positioned off-axis relative to the light source.

Other objects and advantages of the invention will be set forth in the following specification.

BRIEF DESCRIPTION OF THE DRAWINGS

A preferred embodiment of the present invention is illustrated in the accompanying drawings, wherein:

FIG. 4 is an elevational view of the reversion prism incorporated in the present invention showing the path of two representative light rays;

FIG. 5 is a view similar to FIG. 4 but with the prism rotated 90° counter clockwise from the position of FIG. 4; and FIG. 6 is a block diagram of the electronic circuit associated with the lens-prism optical system associated with the present container inspection apparatus.

DETAILED DESCRIPTION OF THE INVENTION

Figures 1, 1A:
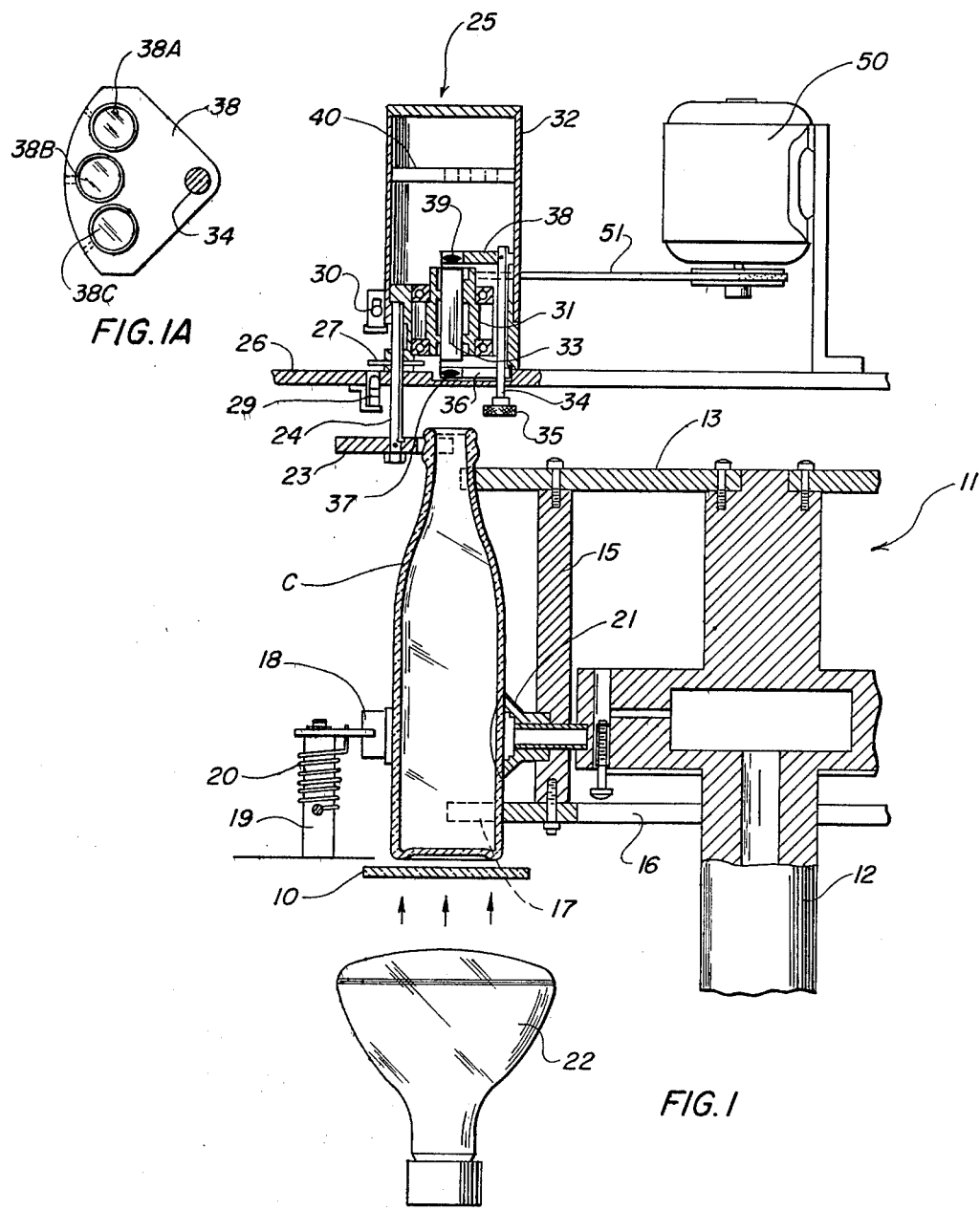
FIG. 1 is a fragmentary sectional elevational view of apparatus by which the present invention may be put into practice.
FIG. 1A is a view of a typical holder for a plurality of lens cooperatively associated with the optical system of the invention.

Reference will first be directed to FIG. 1 wherein the various components of apparatus, located in the area of the inspection station where containers must pass, are shown to best advantage. It is of course recognized that the containers C are transported on a suitable conveyor illustrated at 10 is a high speed and substantial continuous stream as is well understood in the art of conveying containers. In order to stabilize the motion of the containers during transit through the inspection station, a star wheel assembly 11 is provided and is made up of a driven shaft 12 carrying an upper star wheel 13 formed with peripheral recesses 14 which engage the neck portion of each container. The star wheel 13 is provided with a suitable depending structure 15 to which has been attached at the lower end thereof a second star wheel 16 formed with suitable peripheral recesses 16 adapted to engage the side wall of the containers above the heel thereof. Guide means in the form of a fence 18 is provided to retain the stream of containers C in position in the recesses 14 and 17 of the respective star wheels 13 and 16 during the travel through the inspection station. The fence 18 is supported from one or more posts 19 and resilient means 20 is employed to permit the guide means 18 to flex sufficiently during the passage of the containers.

As has been disclosed in a prior U.S. Pat. No. 2,800,226 issued July 23, 1957, the apparatus 11 includes vacuum means associated with a suction cup 21 aligned with each of the peripheral recesses 17 in the lower star wheel 16. The suction cups 21 are adapted to grip the side wall of the containers during passage through the inspection station, and if a container is to be rejected, it is removed from the line of containers on the conveyor 10, the vacuum applied by the suction cup 21 is continued to be applied so that the designated container for rejection is removed from the conveyor 10 at a place beyond the station where actual inspection has taken place.

The inspection station is provided with a radiant energy source 22 which may be a high intensity source of light directed upwardly through the portion of the conveyor 10 which may consist of an opalized glass plate for the passage of the radiant energy in a diffused condition so as to give substantial even light distribution and to eliminate false detection which may arise by reason of lettering or other identifying symbols molded into the bottom and lower side walls of the containers. The apparatus also includes the provision of a small star wheel 23 located in a position to be engaged by the neck portion of each container as it passes through the inspection station. The star wheel 23 is rotatably supported on a shaft 24 which is rotatively carried in a suitable head assembly 25. The shaft, at a place above a platform 26, supports a disk 27 which is formed with a series of radial slots 28. The radial slots 28 formed in the disk 27 are positioned so that they will pass through the path of a light beam generated by the light 29 which directs its beam onto a photocell 30. Each container C which engages and rotates the star wheel 23 rotates the shaft 24 and causes rotation of the disk 27, and this moves a slot through the path of the light beam from the source 29 so that the photocell 30 is energized to generate a signal indicating the presence of a container in position for inspection.

The head assembly 25 is carried by the platform 26 and is adapted to support a holder device 31 rotatably mounted in the housing 32 and positioned to support a reversion prism device 33. The housing 32 also carries a shaft 34 having a control knob exposed for suitable manipulation of the shaft 34. A lens holder 36 is keyed to the shaft 34 in position to hold lens means 37 in the axis of the radial energy passing through the container apparatus during the inspection. The shaft 34 also carries a second holder 38 which carries lens means 39 in position to focus the light passing through the prism 33 onto a support 40 which carries an array of photocells or radiant energy responsive elements 41, 42 and 43 which are shown in more detail in FIG. 6.

The lens holders 36 and 38 are each arranged to carry a plurality of lenses which have different characteristics of cooperation with the prism 33 to take care of variations in the requirements of inspection of containers having different physical characteristics. One typical arrangement of holder 38 carrying a plurality of lenses 38A, 38B and 38C which are shown in FIG. 1A, and it is understood that the holder 36 would be similarly constructed to present lenses compatible with those in the holder 38.

As seen in FIGS. 4 and 5 the prism 33 is formed with opposite end faces 43 and 44 in substantial axial alignment for the entry and exit of light rays, depicted at A and B. The body of the prism 33 is formed with an off set portion 45 at one side, and with angularly related flat surfaces 46 and 47 at the opposite side. The apex 48 where these flat surfaces meet is spaced from and substantially centered to the flat surface 49 in the opposite off-set portion 45. The angular surfaces 46 and 47 are polished so the interior of each thereof is presented as a reflecting face, and the surface 49 is polished or treated by silvering to present its interior as a mirror. The action of the surfaces 46, 47 and 49 is such that in the position of the prism 33 in FIG. 4, the light rays A and B entering at end 43 are reversed by 180° upon exiting at end 44. When the prism 33 is viewed from a position 90° to the position of FIG. 4 where the flat surfaces 46 and 47 are presented face up, as seen in FIG. 5, the light rays A and B are seen to have parallel paths. The normal action of the prism 33 is to cause an image to rotate twice for each complete rotation of the prism. Thus for 360° of prism rotation, the object is rotated by 720°.

Figure 2B:
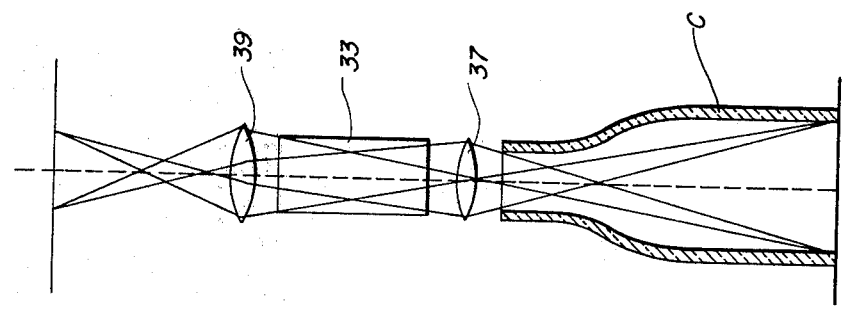
FIGS. 2A and 2B are schematic illustrations respectively of the prior art optical system and of the presently improved optical system illustrating the limitations of the prior art by comparison.
Figure 2A:
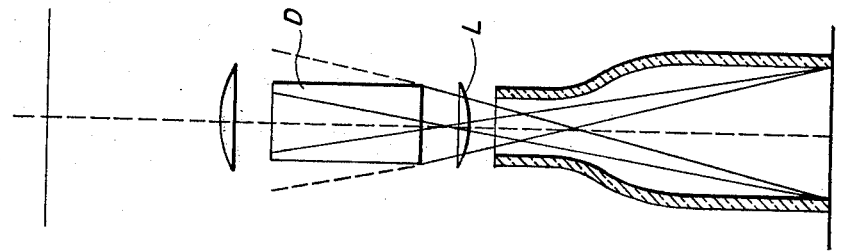

Certain advantages of the present invention can be seen upon comparing the prior art lens-prism system of FIG. 2A with the preferred system of FIG. 2B. In FIG. 2A, the lens L in front of the Dove prism D for collimating the lighted image of the container bottom is too weak to retain the far-off-axis areas of the container bottom object. Thus a substantial portion of the area being inspected is lost to the photosensitive means in support 40 positioned at the image plane. In FIGS. 2A and 2B the inspection is performed at the time when the central axis of the container coincides with the optical axis, but as shown the Dove prism and lens system of FIG. 2A does not have the ability to gather light from far-off-axis objects. The lens prism system of FIG. 2B possesses the ability to gather in the far-off-axis objects and retain the light to present to the photosensitive means located at the image plane. This advantage is obtained due to the ability of the reversion prism to rotate non-collimated light rays without introducing distortion; this ability derives from the use of reflective surfaces to preserve the "non-diverted line-of-sight" character of the prism. By contrast, the Dove prism of the prior art uses refractive surfaces to preserve this characteristic, and hence must be placed in a beam of light which has been collimated. An example of the characteristics of the subject prism which has been referred to above, it is important to form the reversion prism 33 in accordance with the following characteristics: the aspect ratio of the prism must be such as to relate the relationship between the length of the side of the end face 43 or 44 and the overall length of the prism between the end faces to an optimum value, as for example a value of 0.25; and to form the obtuse angle between the surfaces 46 and 47 at a value approaching 127°; and finally to maintain the distance between the apex 48 and the off-set surface 49 at approximately ⅓ the overall length of the prism between the end faces 43 and 44. The aspect ratio is important because it will determine the overall configuration of the prism which must be considered in order to be able to keep it within a manageable size for purposes of rotation. For a given end face width as the extent of the off-set portion is decreased, the prism becomes awkwardly long, and conversely as the prism length is decreased the extent of the off-set portion gets awkwardly big so as to make it difficult to fit it into a convenient size of apparatus. A further characteristic for the prism 33 is that it must be selected from material that will permit maximum transmission of light, and therefore it is preferred to make the prism of optical crown glass thereby satisfying the light transmission capability.

Figure 3B:
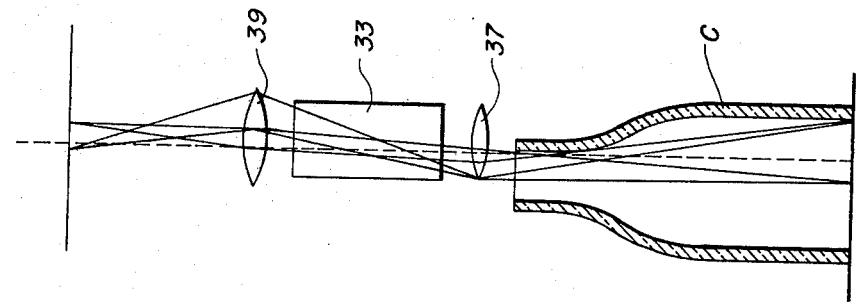
FIGS. 3A and 3B are schematic illustrations respectively of the prior art optical system in relation to off-axis alignment of the container and of the presently improved optical system under the same off-axis alignment of the container.
Figure 3A:
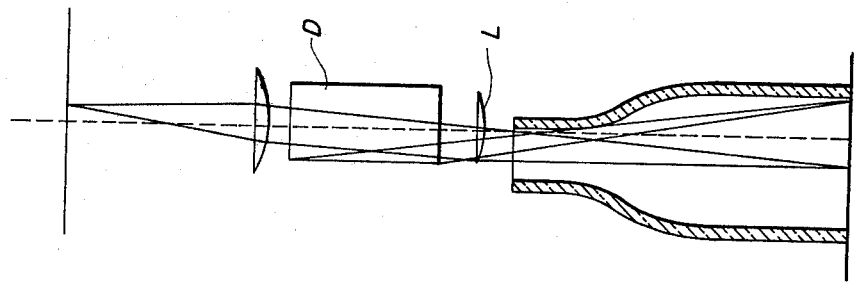

In the prism-lens prior art system of FIG. 3A, when the prism D rotates the container bottom image past the array of photosensitive means in the image plane, the presence of foreign matter located precisely at the bottom center cannot be detected unless the container is displaced off-axis. Thus, the inspection is typically taken before the container axis reaches the optical axis. When this practice is followed light level discrepancies arise in the prism D which causes AC waveforms at the photosensitive means and that produces false detection signals. The system seen in FIG. 3B has the advantage in that the strong objective lens 37, which is permitted by the reversion prism 33, holds light levels uniform at the image plane and so false signals are precluded.

It is understood that the rotation of the prism 33 is accomplished in any suitable manner, such as by motor 50 having a belt connection 51 with the holder device 31 (see FIG. 1). As shown in FIG. 4 and 5 the rotation of the prism 33 causes the light rays to rotate. The result is that the lighted bottom of the container is projected by the lens-prism system 37, 33 and 39 upon the photosensitive means 41, 42 and 43. As the bottom image rotates past the photosensitive means, any dark spot caused by foreign matter will generate an impulse due to a change in the level of the light intensity.

As seen in FIG. 6, the impulse signal from any one of the sensitive means 41, 42 or 43 is processed in the respective amplifiers 52, 53 and 54 and compared to a selected threshold voltage from source 55. The voltage source 55 is connected to comparators 56, 57 and 58. These comparators are connected to adjustable signal level control circuits 59, 60 and 61 to facilitate balancing. If a compared signal is greater than the selected threshold level, the affected comparator applies an output signal to one-half of an AND gate 62, 63 or 64. The other half of the AND gate that is affected is controlled by a timing interval generator 65 triggered by the signal from the photocell means 30 which announces the presence of a container in position for inspection. The generator 65 is energized for a specific interval which is typically equal to the 180° scan time of the prism 33 coincidental with the centering of the container C in the lens-prism optical system. Which ever AND gate is affected it applies an output signal from the photosensitive circuit and drives a suitable reject actuator 67 to remove the container.

The improvement described above has the unique feature that the reversion prism 33 does not depend on plane wave fronts from the light source for its proper performance, as does the Dove prism of prior systems. Hence the reversion prism places no restrictions on the strength of the object lens 37. This freedom permits a widening of the field of view and stabilizes the function of the lens-prism system in the presence of container misalignment, whether it be intentional or unintentional, compared to the prior art collimation lens-prism system. The improved results are that a more dependable detection of foreign matter at the central area of the container bottom is obtained, as well as in peripheral areas of containers which have large diameters for the vertical height relation (sometimes called squatty containers). The improved system also improves the sensitivity of inspection so that breaks in lower container side walls can be detected.

What is claimed is:

1. Apparatus for inspecting open mouth containers for foreign matter comprising: means supporting a container at an inspection station; a source of illumination for lighting the container through the bottom thereof; an array of light sensitive means spaced opposite the open mouth of the container for generating signals proportional to the level of light intensity received by each thereof; a lens-prism system disposed between the open mouth of the container and said array of light sensitive means for directing the image of the lighted area of the container upon said array of light sensitive means, said lens-prism system including a reversion prism, and a convex object lens and a convex image lens cooperating with said prism; circuit means connected to said array of light sensitive means for processing the signals therefrom, said circuit means having means to establish a threshold signal level; means connected to said circuit means for rejecting a container producing a signal greater than said established threshold signal level; and means adjacent to the inspection station for initiating the inspection of a container in the inspection station.

2. The apparatus set forth in claim 1, wherein said reversion prism presents three interior reflecting surfaces to the passage of light, said surfaces being angularly related to each other for effecting a 180° reversal in the transmission of the lighted image of the container.

3. The apparatus set forth in claim 1, wherein said reversion prism has an axis of elongation aligned with the focal axis of said object and imaging lenses, and means is connected to said prism for rotating the same about its axis of elongation.

4. The apparatus set forth in claim 1, wherein drive means is connected to rotate said prism for rotating the lighted image of the container projected by said convex object lens substantially free of plane wave fronts from the light source.

5. Apparatus for inspecting open mouth containers for foreign matter, said apparatus comprising: conveyor means for moving a series of containers through an inspection station; a source of radiant energy directed through the bottom area of the containers at the inspection station; an array of radiant energy sensitive means spaced from the open mouth of the containers in the inspection station in positions for generating signals proportional to the levels of radiant energy received from said source of radiant energy through the containers; an optical system disposed between the container open mouth and said array of radiant energy sensitive means, said system including a reversion prism having opposite end faces substantially parallel with each other and being mounted for rotation about an axis passing through said opposite end faces, said prism having said axis substantially coincident with the inspection station, a cooperating objective lens in position for gathering the radiant energy directed through the bottom area of the containers at the inspection station, and an imaging lens in position for focusing the radiant energy from said reversion prism upon said array of radiant energy sensitive means; means for rejecting containers; and an operating circuit connected between said rejecting means and said array of radiant energy sensitive means, said operating circuit including means establishing a threshold signal level for acceptable containers, means for comparing the signals from said radiant energy sensitive means with said established threshold signal, and signal output means from said comparing means connected to said reject means for operating the latter means.

6. The apparatus set forth in claim 5, wherein said operating circuit also includes signal amplifiers for each of said radiant energy sensitive means in said array thereof, and means connected to each amplifier for balancing the signal levels emitted by said amplifiers.

7. The apparatus set forth in claim 5, wherein means is connected into said operating circuit for generating a signal each time a container reaches the inspection station.

8. The apparatus set forth in claim 7, wherein said signal generating means includes time measuring means establishing container scan time by said optical system substantially equal to at least one-half rotation of said reversion prism.

* * * * *